United States Patent [19]
Klein et al.

[11] Patent Number: 5,618,779
[45] Date of Patent: Apr. 8, 1997

[54] TRIGLYCERIDE-BASED BASE OIL FOR HYDRAULIC OILS

[75] Inventors: Johann Klein; Frank Bongardt, both of Duesseldorf; Peter Daute, Essen; Matthias Fies, Krefeld, all of Germany

[73] Assignee: Henkel Kommanditgesellschaft auf Aktien, Duesseldorf, Germany

[21] Appl. No.: 581,571

[22] PCT Filed: Jul. 6, 1994

[86] PCT No.: PCT/EP94/02212

§ 371 Date: Feb. 8, 1996

§ 102(e) Date: Feb. 8, 1996

[87] PCT Pub. No.: WO95/02659

PCT Pub. Date: Jan. 26, 1995

[30] Foreign Application Priority Data

Jul. 15, 1993 [DE] Germany .................. 43 23 771.1

[51] Int. Cl.$^6$ .................. C10M 107/34; C10M 101/04
[52] U.S. Cl. .................. 508/486; 508/491
[58] Field of Search .................. 508/486, 491, 508/497

[56] References Cited

U.S. PATENT DOCUMENTS

| | | | |
|---|---|---|---|
| 2,556,145 | 6/1951 | Niederhauser | 508/491 |
| 3,066,159 | 11/1962 | De Groote et al. | 508/491 |
| 3,871,837 | 3/1975 | Bedague et al. | 44/58 |
| 4,783,274 | 11/1988 | Jokinen et al. | 508/497 |
| 5,080,814 | 1/1992 | Awad | 508/497 |
| 5,451,334 | 9/1995 | Bongardt et al. | 252/56 R |
| 5,458,698 | 10/1995 | Bershas et al. | 508/486 |

FOREIGN PATENT DOCUMENTS

| | | |
|---|---|---|
| 0247509 | 12/1987 | European Pat. Off. . |
| 0325010 | 7/1989 | European Pat. Off. . |
| 0458584 | 11/1991 | European Pat. Off. . |
| 0602981 | 6/1994 | European Pat. Off. . |
| 3927155 | 2/1991 | Germany . |
| 1047253 | 11/1966 | United Kingdom . |
| 1050497 | 12/1966 | United Kingdom . |
| 1210509 | 10/1970 | United Kingdom . |
| WO8805808 | 8/1988 | WIPO . |

OTHER PUBLICATIONS

Römpp Chemie–Lexikon, 9. erw. Auflage, (1990), Seite 1878—sonst wie im Recherchericht angegeben month unavailable.

Synthetic Fats by P.N. Williams in "Chemistry and Industry" (London) 19, 1947, p. 251–255 month unavailable.

Primary Examiner—Jacqueline V. Howard
Attorney, Agent, or Firm—Wayne C. Jaeschke; John E. Drach; Henry E. Millson, Jr.

[57] ABSTRACT

Hydraulic oils containing a biodegradable base oil comprising either a) the product of the ethoxylation and/or propoxylation of glycerol with from about 0.5 to about 3 moles of ethylene oxide and/or propylene oxide and subsequent esterification with a saturated or unsaturated $C_{6-24}$ fatty acid, or mixtures thereof; or b) the product of the insertion of from about 0.5 to about 3 moles of EO and/or PO into a natural oil or fat other than castor oil.

16 Claims, No Drawings

TRIGLYCERIDE-BASED BASE OIL FOR HYDRAULIC OILS

BACKGROUND OF THE INVENTION

1. Field of the Invention

This invention relates to a biodegradable triglyceride-based base oil, to its production and to hydraulic oils containing this base oil.

2. Statement of Related Art

In the past, most hydraulic oils were produced from mineral oil. The same is still true today. In applications where the escape of oil into the environment has to be accepted as a possibility, for example through unavoidable leakages, there is an increasing demand for hydraulic oils which contain environmentally friendly ester oils, particularly those based on rapeseed oil and/or soybean oil, as their oil base. Typical applications of the type in question include the machinery and tools used in forestry, agriculture, building and the like. These applications require the use of hydraulic oils belonging to water hazard class 0-1. Ester-based hydraulic oils are capable of meeting these requirements.

However, ester oils of the above-mentioned type essential for practical application, i.e. oils based on purified rapeseed oils and/or soybean oils, more particularly those freed from aminopectins and other slime-forming substances, have two distinct weaknesses in terms of practical application, namely:

Ester oils based on polyunsaturated fatty acid systems tend to thicken rapidly, even at only moderately elevated operating temperatures, for example in the range from 50° to 80° C. The reason for this is the readiness of the olefinic double bonds of the ester-forming acids of the oil type in question to enter into viscosity-increasing reactions in the presence of atmospheric oxygen. Although it is known in principle that such unwanted increases in viscosity in hydraulic oils can be avoided by the addition of antioxidants, it has been found that the antioxidants hitherto preferably used in hydraulic oils based on mineral oils perform unsatisfactorily in ester oils of the type in question.

Another important limitation of hydraulic oils based on the environmentally friendly ester oils mentioned is their inadequate stability at low temperatures. For example, purified rapeseed oil has a solidification point or pour point of $-16°$ C. Even before the solidification point is reached, a remarkable increase in viscosity occurs with decreasing temperatures. The comparatively high pour point of rapeseed oil, for example in winter, poses considerable problems for the practical application of the hydraulic oils at low ambient temperatures. These problems can of course be made considerably worse in practice if, at the same time, the considerable increase in the pour point of the hydraulic oil is initiated by oxidative thickening of the above-mentioned ester oil. The addition of pour point depressants does not solve the technical problem involved. It is known that the effect of pour point depressants disappears after prolonged presence in the oil to be treated.

DE-A-39 27 155 describes an environmentally friendly base oil based on natural substances for the formulation of hydraulic oils containing a rapeseed oil and/or soybean oil as the main oil component, specially selected antioxidants and a quantity equal to the main oil component of esters of trimethylol ethane, trimethylol propane and/or neopentyl alcohol with $C_{5-10}$ monocarboxylic acids or at least partly unsaturated fatty acids based on rapeseed oil, soybean oil or sunflower oil.

DESCRIPTION OF THE INVENTION

The problem addressed by the present invention was to provide base oils for the formulation of hydraulic oils which would show high low-temperature stability without any need for the addition of pour point depressants or synthetic esters.

According to the invention, the problem stated above has been solved by triglyceride-based base oils obtainable by a) ethoxylation and/or propoxylation of glycerol with 0.5 to 3 moles of ethylene oxide (EO) and/or propylene oxide (PO) and subsequent esterification with saturated and/or unsaturated $C_{6-24}$ fatty acids from natural sources or mixtures thereof by methods known per se or b) insertion of 0.5 to 3 moles of EO and/or PO into natural oils or fats by methods known per se.

Preferably 0.5 to 2 moles and, more preferably, 0.5 to 1 mole of EO and/or PO is/are used for the ethoxylation and/or propoxylation of glycerol.

Preferably 0.5 to 2 moles and, more preferably, 0.5 to 1 mole of EO and/or PO is/are preferably used for the insertion of EO and/or PO into the natural oils or fats.

Suitable fatty acid components for the esterification of the reaction products of EO and/or PO with glycerol are unsaturated or saturated $C_{6-24}$ fatty acids from natural sources.

Particularly preferred saturated fatty acids are hexanoic acid (caproic acid), octanoic acid (caprylic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachic acid), docosanoic acid (behenic acid) or tetracosanoic acid (lignoceric acid).

Particularly preferred unsaturated fatty acids are tetradecenoic acid (myristoleic acid), hexadecenoic acid (palmitoleic acid), octadecenoic acid (oleic acid), eicosenoic acid (gadoleic acid), docosenoic acid (erucic acid), 12-hydroxy-octadecenoic acid (ricinoleic acid), octadecadienoic acid (linoleic acid), octadecatrienoic acid (linolenic acid), eicosatetraenoic acid (arachidonic acid) or docosapentaenoic acid (clupanodonic acid).

Coconut oil, palm kernel oil, palm oil, peanut oil, cotton oil, soybean oil, sunflower oil, rapeseed oil rich or poor in erucic acid, castor oil, tallow and fish oil are preferably used for the insertion of EO and/or PO into the natural oils or fats.

The process for the ethoxylation and/or propoxylation of glycerol with ethylene oxide and/or propylene oxide is known per se, cf. the relevant specialist literature.

Adducts of alkylene oxides with glycerol are generally known substances which may be obtained by the relevant methods of preparative organic chemistry. On an industrial scale, they are produced by ethoxylation or propoxylation of glycerol in the presence of basic catalysts, such as for example lithium hydroxide, potassium hydroxide, sodium methylate, strontium phenolate or calcined hydrotalcite, at temperatures in the range from 120° to 180° C. and under pressures of 1 to 5 bar. If mixed alkoxylates are used, the alkoxylation reaction may take place in blocks or at random. After the alkoxylation reaction, the products may be neutralized by addition of acids (phosphoric acid, acetic acid, lactic acid). However, non-neutralized catalysts, especially lithium hydroxide, may also be used for the subsequent esterification step.

The esterification of the reaction product after the ethoxylation and/or propoxylation of glycerol with the saturated or unsaturated $C_{6-24}$ fatty acids mentioned above is also carried out by methods known per se to the expert (cf., for example, *Synthetic fats* by P. M. Williams in "Chemistry and Industry" (London) 19 1947), 253).

The process for the insertion of alkylene oxides, more especially ethylene oxide and/or propylene oxide, is also described in detail in the relevant specialist literature and is carried out in the presence of catalysts, such as in particular lithium hydroxide, calcined hydrotalcite, potassium hydroxide or sodium alkoxylate, cf. EP-A-0 247 509 where the insertion of alkylene oxides into triglycerides is described in detail by further references to the prior art.

Accordingly, by inserting ethylene oxide and/or propylene oxide into natural oils or fats, the pour point of the basic oils/fats can be directly reduced to a considerable extent. It is possible in this way to produce inexpensive hydraulic base oils which have only to be slightly chemically modified in relation to the basic natural oils and fats in order to be able to be significantly improved in regard to their low-temperature stability. However, a surprising feature in this regard is that the viscosity of the ethoxylated and/or propoxylated products hardly differs from that of the basic oils/fats and, in general, is even increased.

Since the processes for the production of the base oils according to the invention are made up of individual process steps known per se, there is no need here for any further particulars.

The oils obtainable by the processes mentioned above may be used as base oils for the formulation of hydraulic oils. These base oils show particularly favorable low-temperature behavior because they are characterized by a particularly low pour point (titer). In addition, they are readily and rapidly biodegradable (CEC L33 T82 Test, $\geq 80\%$).

The present invention also relates to hydraulic oils containing the base oils mentioned above in addition to the usual additives. The hydraulic oils according to the invention are obtainable by intensive mixing of the base oils with the usual additives. Suitable methods for this purpose are known to the expert from the relevant literature.

The hydraulic oils according to the invention contain at least 90% by weight, preferably at least 95% by weight and, more preferably, at least 98% by weight of one of the above-mentioned base oils or a mixture thereof.

The base oils according to the invention and, hence, the hydraulic oil compositions containing them show high low-temperature stability so that there is no need to add additional pour point depressants or synthetic esters for typical applications. The base oils according to the invention show a significantly reduced pour point in relation to the fats/oils on which they are based without any deterioration in their viscosity in relation to that of the basic fats/oils.

To prepare the hydraulic oil from the base oil, other typical components have to be added in known manner. Thus, antioxidants, corrosion inhibitors, extreme-pressure additives, anti-wear additives or, where necessary, other pour point depressants may be added to the base oils according to the invention.

The extreme-pressure additives are, in particular, sulfurized triglycerides, sulfurized fatty acid alkyl esters, sulfurized sperm oils, phosphoric acid esters, such as trioleyl alcohol phosphate or triaryl phosphate.

Particularly suitable anti-wear additives are zinc dialkyl dithiophosphate compounds, such as zinc (di-2-ethylhexyldithiophosphate).

The products marketed as "Edenor" 2410 (by Henkel KGaA, Düsseldorf) and "Viskoplex" (by Röhm, Darmstadt) are mentioned as examples of pour point depressants. These products are polymer-based pour point depressants which infinitely delay crystallization.

Suitable corrosion inhibitors are, in particular, succinic acid semiesters, sorbitan monooleate, amine soaps of long-chain fatty acids. Additin (a product of Rheinchemie, Mannheim), Edenor or Eumulgin (products of Henkel KGaA, Düsseldorf) are mentioned in this connection.

Suitable antioxidants are, in particular, combinations of sterically hindered aromatic compounds, more particularly TBHQ (tert.butyl hydroxyquinoline) or BHT (butoxylated hydroxytoluene), and anionic antioxidants, such as in particular, BHA (butoxylated hydroxyanisole) or phenothiazine (a product of Hoechst AG, Frankfurt). A liquid antioxidant—Edenor VP 2465 (a product of Henkel KGaA, Düsseldorf)—which consists of a combination of anionic and phenolic antioxidants may also be used.

Further information on the particular formulation of hydraulic oils, their additives and the quantities in which they are used can be found in the prior art literature on this class of materials cited in detail in the foregoing.

The following Examples are intended to illustrate the invention without limiting it in any way.

EXAMPLES

1. Preparation of Glycerol Propoxylate Trioleate a) Glycerol propoxylate

In a 4 liter steel autoclave, 0.45 g of lithium hydroxide was added to 2400 g (26 moles) of glycerol. After heating to 80° C., adhering traces of water were removed by evacuation and purging with nitrogen a total of 5 times. The reaction mixture was then heated to 150° C., after which 1500 g (26 moles) of propylene oxide were added in portions so that the pressure in the reactor did not exceed a value of 5 bar. On completion of the reaction (around 3 h), the mixture was cooled to 80° to 100° C. and a vacuum was applied for about 15 minutes to remove traces of unreacted propylene oxide. Around 3900 g of glycerol propoxylate were obtained in the form of a clear colorless liquid with a hydroxyl value of 1200.

b) Glycerol propoxylate trioleate

A mixture of 157.2 g (1.04 mole) of glycerol propoxylate with an OH value of 1113 and 833.2 g (3 moles) of a technical oleic acid with an acid value of 203 and an iodine value of 90 was heated for 2 hours to 240° C. in the presence of 1 g of tin oxalate. The water of condensation formed was distilled off. After heating for another 5 hours at 240° C., the water of condensation was distilled off in a vacuum of 16 mbar. In order to complete esterification of the carboxylic acid, another 2.5 g (0.017 mole) of glycerol propoxylate with an OH value of 1113 was added and the mixture was heated for 3 hours at 240° C. under a vacuum of 16 mbar. The mixture was then cooled to 95° C., 20 g of bleaching earth (based on montmorillonite) were added and filtered off. The product was dark yellow in color and slightly viscous. It had an OH value of 8.9 and an acid value of 0.9.

c) Reaction of rapeseed oil with propylene oxide (insertion)

In a 2 liter steel autoclave, 0.94 g of hydrated lithium hydroxide was added to a mixture of 872 g (1 mole) of rapeseed oil from new plants and 8.7 g (95 mmoles) of glycerol, followed by heating to 100° C. Adhering traces of water were removed by evacuation and purging with nitrogen a total of 5 times. The reaction mixture was then heated to 180° C. and 58 g (1 mole) of propylene oxide were added in portions so that the pressure in the reactor did not exceed a value of 5 bar. On completion of the reaction (approx. 3 h), the reaction mixture was cooled to 80°–100° C. and a vacuum was applied for about 15 minutes to remove traces of unreacted propylene oxide. After neutralization of the catalyst with 2.24 g of 90% lactic acid and filtration, a yellow liquid was obtained in a quantity of around 930 g.

2. Comparison of Glycerol Monopropoxylate (GPO) Trioleate with Rapeseed Oil

1 Mole of glycerol is reacted with 1 mole of propylene oxide. The glycerol monopropoxylate (GPO) formed was esterified with 3 moles of the fatty acid Edenor TiO5 (oleic acid from beef tallow). The product was compared with rapeseed oil.

|  | GPO Trioleate | Rapeseed oil*) |
|---|---|---|
| Acid value (DIN 53402) | 2.4 | 1 |
| Kinemat. viscosity (mm$^2$) (DIN 51562) |  |  |
| at 40° C.: | 43.8 | 38.1 |
| at 100° C.: | 8.98 | 8.51 |
| Viscosity index (DIN ISO 2909) | 192 | 210 |
| Demulsifying power [min.]: (DIN 51599) | >60 | 8 |
| Air separation capacity (min.): (DIN 51381) | 7 | 6 |
| Cloud point (°C.) (DIN ISO 3015) | −21 | −16 |
| Pour point (°C.) | −34 | −17 |

*)Refined rapeseed oil low in erucic acid

We claim:

1. In a hydraulic oil comprising a base oil and at least one of an antioxidant, corrosion inhibitor, extreme-pressure additive, or anti-wear additive, the improvement wherein the base oil comprises either a) the product of the ethoxylation and/or propoxylation of glycerol with from about 0.5 to about 3 moles of ethylene oxide and/or propylene oxide and subsequent esterification with a saturated or unsaturated $C_{6-24}$ fatty acid, or mixtures thereof; or b) the product of the insertion of from about 0.5 to about 3 moles of EO and/or PO into a natural oil or fat other than castor oil.

2. The hydraulic oil of claim 1 wherein the base oil comprises product a).

3. The hydraulic oil of claim 2 wherein the base oil consists of product a).

4. The hydraulic oil of claim 1 wherein the base oil comprises product b).

5. The hydraulic oil of claim 4 wherein the base oil consists of product b).

6. The hydraulic oil of claim 1 wherein the base oil comprises at least about 90% by weight of the hydraulic oil.

7. The hydraulic oil of claim 6 wherein said quantity is at least about 95% by weight of the hydraulic oil.

8. The hydraulic oil of claim 6 wherein said quantity is at least about 98% by weight of the hydraulic oil.

9. The hydraulic oil of claim 1 wherein in product a) from about 0.5 to about 2 moles of EO and/or PO are used for the ethoxylation and/or propoxylation.

10. The hydraulic oil of claim 1 wherein in product b) from about 0.5 to about 2 moles of EO and/or PO are inserted into the natural oil or fat.

11. The hydraulic oil of claim 1 wherein in product a) the saturated or unsaturated $C_{6-24}$ fatty acid or mixture thereof is at least one of caproic acid, caprylic acid, capric acid, lauric acid, myristic acid, palmitic acid, stearic acid, arachic acid, behenic acid, lignoceric acid, myristoleic acid, palmitoleic acid, oleic acid, gadoleic acid, erucic acid, ricinoleic acid, linoleic acid, linolenic acid, arachidonic acid or clupanodonic acid.

12. The hydraulic oil of claim 1 wherein in product b) the natural fat or oil is coconut oil, palm kernel oil, palm oil, peanut oil, cotton oil, soybean oil, sunflower oil, rapeseed oil rich or poor in erucic acid, tallow, or fish oil.

13. The hydraulic oil of claim 1 wherein in product a) from about 0.5 to about 1 mole of EO and/or PO are used for the ethoxylation and/or propoxylation.

14. The hydraulic oil of claim 1 wherein in product b) from about 0.5 to about 1 mole of EO and/or PO are inserted into the natural fat or oil.

15. The hydraulic oil of claim 1 wherein in product a) the $C_{6-24}$ fatty acid is a mixture of fatty acids obtained from a natural source.

16. The hydraulic oil of claim 1 which is free from pour point depressants.

* * * * *